(12) United States Patent
Anderson et al.

(10) Patent No.: US 11,213,301 B2
(45) Date of Patent: Jan. 4, 2022

(54) SURGICAL TOOL RELEASE MECHANISM

(71) Applicant: DEPUY IRELAND UNLIMITED COMPANY, County Cork (IE)

(72) Inventors: James Anderson, Batley (GB); Alec Birkbeck, Leeds (GB); Ian Flatters, Penistone (GB); David Horne, Leeds (GB)

(73) Assignee: DePuy Ireland Unlimited Company, Ringaskiddy (IE)

( * ) Notice: Subject to any disclaimer, the term of this patent is extended or adjusted under 35 U.S.C. 154(b) by 203 days.

(21) Appl. No.: 16/629,455

(22) PCT Filed: Jun. 26, 2018

(86) PCT No.: PCT/EP2018/067076
§ 371 (c)(1),
(2) Date: Jan. 8, 2020

(87) PCT Pub. No.: WO2019/011647
PCT Pub. Date: Jan. 17, 2019

(65) Prior Publication Data
US 2020/0163683 A1    May 28, 2020

(30) Foreign Application Priority Data
Jul. 12, 2017 (GB) ..................................... 1711177

(51) Int. Cl.
*A61B 17/00* (2006.01)
*A61B 17/16* (2006.01)

(52) U.S. Cl.
CPC ...... *A61B 17/1617* (2013.01); *A61B 17/1633* (2013.01); *A61B 17/1666* (2013.01); *A61B 2017/00473* (2013.01); *A61B 2017/00477* (2013.01)

(58) Field of Classification Search
CPC combination set(s) only.
See application file for complete search history.

(56) References Cited

U.S. PATENT DOCUMENTS

2005/0124981 A1* 6/2005 Desarzens .......... A61B 17/1666
606/1

OTHER PUBLICATIONS

EP International Search Report for PCT/EP2018067076 dated Nov. 27, 2018.

* cited by examiner

*Primary Examiner* — Sameh R Boles
(74) *Attorney, Agent, or Firm* — Cynthia K. Barnett

(57) ABSTRACT

The invention provides a reamer handle comprising: a shank having a distal tool coupling end adapted to releasably couple to a part of a surgical tool and a proximal end; a retractable catch which is linearly displaceable along the shank between a non-retracted position in which the catch captures the surgical tool within the distal tool coupling end of the tool holder and a retracted position in which the catch enables the tool to be released from the distal tool coupling end; a biasing member configured to bias the catch in the non-retracted position; and a sleeve extending along the shank. The sleeve comprises: a distally located catch contacting portion and a proximally located handle portion for manually displacing the sleeve relative to the shank such that displacement of the catch contacting portion moves the retractable catch between the non-retracted position and the retracted position to enable capture and release of the tool from the tool holder.

18 Claims, 13 Drawing Sheets

SURGICAL TOOL RELEASE MECHANISM

This application is a National Stage Application filed Under 35 U.S.C. § 371 of International Application No. PCT/EP2018/067076 filed Jun. 26, 2018, which claims priority to GB1711177.4 filed Jul. 7, 2017, which is hereby incorporated by reference in its entirety

FIELD OF THE INVENTION

The present invention is in the field of surgical instruments which are used to assist in the removal, repair or replacement of tissue. In particular, the present invention relates to a sleeve for use with a reamer handle to facilitate coupling and uncoupling of surgical tools, such as an acetabular grater, during surgery. There is also provided kits including the sleeve and surgical methods of use thereof.

BACKGROUND TO THE INVENTION

The surgical process for implanting artificial hip joints includes the use of a tool commonly known as an acetabular grater. The acetabular grater is used for reaming the inner surface of the acetabular socket to create a surface within the socket that is suitable for accommodating the installation of a generally concave, artificial acetabular cup and liner. A typical acetabular grater is comprised of a modular metal shell component, having a convex, substantially hemispherical geometrical configuration. A shell component, which is the acetabular grater, typically is mounted to a long metal shaft commonly known as a reamer handle, which connects along the central part of the cavity located on the backside of acetabular grater. The reamer handle forms an axis of rotation for the acetabular grater. A source of rotary power in the form of a surgical drill is connected to the reamer handle and turns the rotating portion of the reamer handle along with the acetabular grater, thus allowing the surgeon to transmit torque to achieve the cutting and grating of bone and cartilage within the joint socket.

Cutting of bone is achieved via a plurality of sharp, raised edges located along the convex surface of the acetabular grater.

Each shell component grater has a designated diameter. Based upon the size of the patient's natural joint socket, reaming begins with the use of an acetabular grater that is smaller than the natural joint socket, and then progresses incrementally in size until all the joint cartilage or other soft tissue or bony debris is removed, and the acetabulum is reamed to the desired size and condition. As each shell of the grater fills with bone and cartilage fragments during the reaming process, they are extracted from the joint, then the grater is changed to a larger size, and reaming resumes. The features and functions of an acetabular reaming system and all its components are known to those of ordinary skill in the art, and thus need not be described in further detail herein.

Surgical staff currently face several challenges when using acetabular grater drivers. Due to the distal location of the grater attachment/release mechanism it is often difficult to efficiently couple and uncouple the acetabular grater to the reamer handle. This is particularly problematic when the surgeon wishes to exchange the acetabular grater within the surgical site. Furthermore, the advent of new styles of surgical approaches have placed further demands on traditional instruments used during orthopaedic procedures, such as during total hip arthroplasty or replacement. The design of the conventional reamer handles often hinders access to the grater release mechanism if a surgeon favours a more minimally invasive surgical approach. Additionally, in terms of safety, it would be desirable for a surgical assistant to be able to activate the grater attachment/release mechanism "remotely" from the rotating acetabular reamer.

Reamer handles have a distal tool coupling end which can be used to couple the handle to a surgical tool, such as an acetabular grater. Reamer handles are provided in straight-handled and off-set versions. In the straight-handles version a proximal end of an inner tube is telescopically received within a distal end of an outer tube section. In some instances, the inner tube section can be inadvertently disassembled from the outer tube section.

The sleeve of the present invention transfers the surgical tool attachment and release mechanism from the distal end of the reamer handle to a position on the handle that is closer to where the surgeon grips the handle during use. The sleeve is compatible with both straight and offset styles of reamer handles that are commercially available.

It is envisaged that the sleeve can supplied as a stand-alone attachment. This enables the sleeve to be retrofitted to an existing reamer handle, as and when required. Alternatively, the sleeve may be supplied pre-fitted to a reamer handle.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to a first aspect of the invention there is provided a reamer handle comprising:
- a shank having a distal tool coupling end adapted to releasably couple to a part of a surgical tool and a proximal end;
- a retractable catch which is linearly displaceable along the shank between a non-retracted position in which the catch captures the surgical tool within the distal tool coupling end of the tool holder and a retracted position in which the catch enables the tool to be released from the distal tool coupling end;
- a biasing member configured to bias the catch in the non-retracted position; and
- a sleeve extending along the shank, the sleeve comprising:
  - a distally located catch contacting portion and
  - a proximally located handle portion for manually displacing the sleeve relative to the shank such that displacement of the catch contacting portion moves the retractable catch between the non-retracted position and the retracted position to enable capture and release of the tool from the tool holder.

The sleeve may wrap entirely around a length of the shank. Alternatively, the sleeve may only partially wrap around the shank. This latter construction reduces the footprint of the sleeve. This reduces amongst other things: the weight of the sleeve, the material costs of the sleeve and the time of manufacture of the sleeve. Advantageously, this reduced footprint minimises any visual obstruction caused by the use of the sleeve. In other constructions, a part of the sleeve may wrap entirely around the shank, whereas other parts of the sleeve may have cut-out sections which provide clearance for portions of the shank to extend through.

The sleeve may include a bridge portion extending between the distally located catch contacting portion and the proximally located handle portion.

A design consideration for the bridge portion is that it has a thin profile. This prevents a "bulky" feel experienced by the surgeon. This also minimises the likelihood of the bridge portion becoming snagged on any tissue within the surgical site.

This bridge portion functions to cradle the shank. In some constructions, the bridge portion of the sleeve may be configured as a trough. The trough may have a profile which generally corresponds to a part of the outer profile of the shank of the surgical tool along which the sleeve is arranged.

For example, in constructions of the reamer handle in which the shank has a substantially circular cross-section when viewed from either the distal end or the proximal end, the bridge portion is configured as a substantially semi-circular trough.

Advantageously, the bridge portion is dimensioned such it overlies cleaning slots provided in the reamer handle. This prevents tissue debris from clogging the slots during use of the reamer handle.

In some constructions of the sleeve for use with an offset reamer handle, the bridge portion may include at least one bend that corresponds to at least one bend in the reamer handle shank.

The proximally located handle portion of the sleeve is preferably ergonomically designed. The handle portion may comprise a flange. The flange may be semi-circular. The flange may include depressions configured for receipt of a user's fingers. This helps the user to gain purchase on the sleeve, and apply a proximally directed linear force. When a user applies a sufficient force to overcome the force of the biasing member, the distally located catch contacting portion is proximally displaced. A consequence of this is that the retractable catch is moved from the non-retracted position (to which it is biased) to the retracted position.

When the user removes the proximally directed force from the proximally located handle portion of the sleeve, the distally located catch contacting portion automatically reverts to the non-retracted position.

The entire sleeve or at least part of the sleeve may be removably attachable to the shank of the reamer handle.

Optionally, at least a part of the sleeve is configured for a snap-fit connection with the shank of the reamer handle. For example, the distally located catch contacting portion and/or the proximally located handle portion of the sleeve may be configured for a snap-fit connection to the shank. The handle portion may be configured as a flexible clip, which can be easily clipped in place about the shank. For example, the flexible clip may be in the form of a substantially semi-circular flange. The flexibility of the clip facilitates the attachment of the handle portion of the sleeve to reamer handles having different sizes of girth. This is advantageous, because it allows a single size of sleeve to be provided within a kit and retrofitted onto different reamer handles.

In some constructions, the shank of the reamer handle (which may also be referred to as the driver body) includes an elongate slot that extends through the exterior surface of the shank. A drive line may be inserted into and removed from the driver body via this slot. Advantageously, the sleeve also functions as a lid for this slot.

In some constructions, the sleeve may comprise at least two portions that are connected by a hinge.

Optionally, the first portion of the sleeve comprises the distally located catch contacting portion and the second portion comprises the proximally located handle portion.

Advantageously, a user may swing the second portion of the sleeve towards or away from the shank by movement about the hinge. This enables the user to temporarily disconnect the second portion of the sleeve from the shank, which facilitates access to the elongate slot and hence the drive line. The drive line can therefore be easily and swiftly replaced.

In some constructions, the first portion consists of the distally located catch contacting portion.

Advantageously, the sleeve is configured such that the sleeve can be connected to the shank in more than one position. This increases surgical choice and minimises the risk that the use of the sleeve, whilst providing benefits to some aspects of the surgery, causes potential drawbacks to other aspects of the surgical process.

At least a part of, or all of the sleeve may be made of made of a plastic, for example a polymer. The use of a plastic limits the increase in weight of the reamer handle caused by the provision of the sleeve. This helps to ensure that the attachment of the sleeve onto the reamer handle does not adversely affect the user experience.

Optionally, at least part of, or all of the sleeve is made of a polymer-coated metal.

In some constructions of the surgical tool, the retractable catch comprises a collar and the distally located catch contacting portion of the sleeve contacts at least part of the collar.

Optionally, the collar is substantially annular and the distally located catch contacting portion of the sleeve is substantially annular or semi-annular. The annular distally located catch contacting portion of the sleeve may be dimensioned such that it encircles at least part of annular collar.

The collar on some reamer handles may include circumferentially-arranged grooves on the exterior surface. In some constructions of the sleeve, the interior surface of the annular distally located catch contacting portion may be configured to grip these circumferential grooves.

In some other constructions, the collar has a shank facing surface and the distally located catch contacting portion of the sleeve contacts at least part of the shank facing surface of the retractable catch. Optionally, the shank facing surface of the retractable catch includes a groove and the distally located catch contacting portion of the sleeve is adapted to engage within this groove. For example the distally located catch contacting portion may include a rim portion which is configured to be received in the internal groove of the retractable catch. In such a constructions, the distally located catch contacting portion of the sleeve is located at least partially internal with respect to the retractable catch.

An important safety consideration is that the remote actuation mechanism for the uncoupling of the surgical tool is not inadvertently activated, particularly during surgery. A safety button may therefore provided on the sleeve.

In a first configuration of the safety button, linear displacement of the sleeve is prevented. So, even if a surgeon accidentally pulls on the handle portion during surgery, the sleeve will not be able to be displaced in the proximal direction. This prevents the retractable catch being moved from the non-retracted to the retracted position. This minimises the likelihood that a surgical tool might be accidentally uncoupled from the reamer handle during surgery.

When a surgeon wishes to uncouple the surgical tool, s/he must place the safety button into its second configuration. In this second configuration, the sleeve is able to be linearly displaced relative to the shank.

The shank may also be provided with a stop to limit the amount of linear displacement of the sleeve in relation to the shank. Optionally, the stop limits the amount of displacement of the sleeve in the proximal direction. This prevents overload at the distal catch interface. Advantageously, the stop limits the linear displacement both the proximal and distal direction. This prevents overload at the distal catch interface in both directions.

In some constructions, the surgical tool coupled to the reamer handle an acetabular grater.

According to a second aspect of the invention, there is provided a sleeve for releasable attachment to a shank of a reamer handle, the sleeve comprising:
  a distally located catch contacting portion for contacting a distally located retractable catch on the tool holder, said catch being linearly displaceable along the shank between a non-retracted position in which the catch captures a surgical tool within a distal tool coupling end of the shank of the tool holder and a retracted position in which the catch enables the tool to be released from the distal tool coupling end, and
  a proximally located handle portion for manually displacing the sleeve relative to the shank of the reamer handle such that displacement of the catch contacting portion moves the retractable catch between a non-retracted position in which the catch captures the tool within the distal tool coupling end of the tool holder and a retracted position to enables the tool to be released from the distal tool coupling end of the tool holder.

The aforementioned disclosure concerning the sleeve as a component of the reamer handle according to the first aspect of the invention is also of relevance for the sleeve according to the second aspect of the invention.

According to a third aspect of the invention, there is provided a kit comprising:
  (i) a reamer handle comprising:
    a shank having a distal tool coupling end adapted to releasably couple to a part of a surgical tool and a proximal end;
    a retractable catch which is linearly displaceable along the shank between a non-retracted position in which the catch captures a surgical tool within the distal tool coupling end of the tool holder and a retracted position in which the catch enables the tool to be released from the distal tool coupling end;
    a biasing member configured to bias the catch in the non-retracted position; and
  (ii) a sleeve configured to be releasably attached to the shank of the reamer handle, the sleeve comprising:
    a distally located catch contacting portion for contacting the retractable catch on the reamer handle, and
    a proximally located handle portion for manually displacing the sleeve relative to the shank such that displacement of the catch contacting portion moves the retractable catch between a non-retracted position in which the catch captures a tool within a distal tool coupling end of the tool holder and a retracted position in which the catch enables the tool to be captured and released from the distal tool coupling end of the tool holder.

The kit of the present invention may also comprise a surgical tool having a reamer handle connection portion that is adapted to be releasably connected to the distal tool coupling end of the reamer handle.

According to a fourth aspect of the invention there is provided a method of releasably coupling a surgical tool to a reamer handle, the method comprising:
  (a) using reamer handle which comprises:
    a shank having a distal tool coupling end adapted to releasably couple to a part of a surgical tool and a proximal end;
    a retractable catch which is linearly displaceable along the shank between a non-retracted position in which the catch captures the surgical tool within the distal tool coupling end of the tool holder and a retracted position in which the catch enables the tool to be released from the distal tool coupling end;
    a biasing member configured to bias the catch in the non-retracted position; and
    a sleeve extending along the shank, the sleeve comprising:
      a distally located catch contacting portion and
      a proximally located handle portion for manually displacing the sleeve relative to the shank such that displacement of the catch contacting portion moves the retractable catch between the non-retracted position and the retracted position to enable capture and release of the tool from the tool holder; and
  (b) using the proximally located handle portion of the sleeve to manually displace the sleeve in a proximal direction along the shank to proximally displace the catch contacting portion of the sleeve and thereby move the retractable catch from the non-retracted position to the retracted position; and
  (c) coupling or uncoupling the surgical tool.

The surgical tool that is releasably coupled to the reamer handle in the above-mentioned method may be an acetabular grater.

Optionally, the above described method of releasably coupling a surgical tool to a reamer handle may be performed by two people. For example, a first person (e.g., a surgical assistant) may use the proximally located handle portion of the sleeve to manually displace the sleeve in a proximal direction along the shank to proximally displace the catch contacting portion of the sleeve, and a second person (e.g., a surgeon) may the couple or uncouple a surgical tool from the distal end of the reamer handle. This is advantageous during minimally invasive surgery, where the space at the surgical site is restricted. This is also advantageous, as it prevents a surgical assistant from having to place their hands near to a rotating cutting tool, which may be inadvertently activated.

According to a fifth aspect of the invention, there is provided a method of releasably coupling a surgical tool to a reamer handle, the method comprising:
  (a) using reamer handle which comprises:
    a shank having a distal tool coupling end adapted to releasably couple to a part of a surgical tool and a proximal end;
    a retractable catch which is linearly displaceable along the shank between a non-retracted position in which the catch captures the surgical tool within the distal tool coupling end of the tool holder and a retracted position in which the catch enables the tool to be released from the distal tool coupling end;
    a biasing member configured to bias the catch in the non-retracted position;
  (b) attaching a sleeve according to the third aspect of the invention to the shank of the reamer handle;
  (c) using the proximally located handle portion of the sleeve to manually displace the sleeve in a proximal direction relative to the shank, thereby displacing the catch contacting portion of the sleeve and moving the retractable catch from the non-retracted position to the retracted position; and
  (d) coupling or uncoupling the surgical tool.

The surgical tool that is releasably coupled to the reamer handle in the above-mentioned method an acetabular grater.

BRIEF DESCRIPTION OF THE DRAWINGS

Constructions of the reamer handle and sleeve for use there with will be described hereinafter, by way of example only, with reference to the accompanying drawings in which like reference signs relate to like elements and in which.

Conventional assemblies of reamer handles and acetabular graters are generally known to a person skilled in the art.

Figure 1:
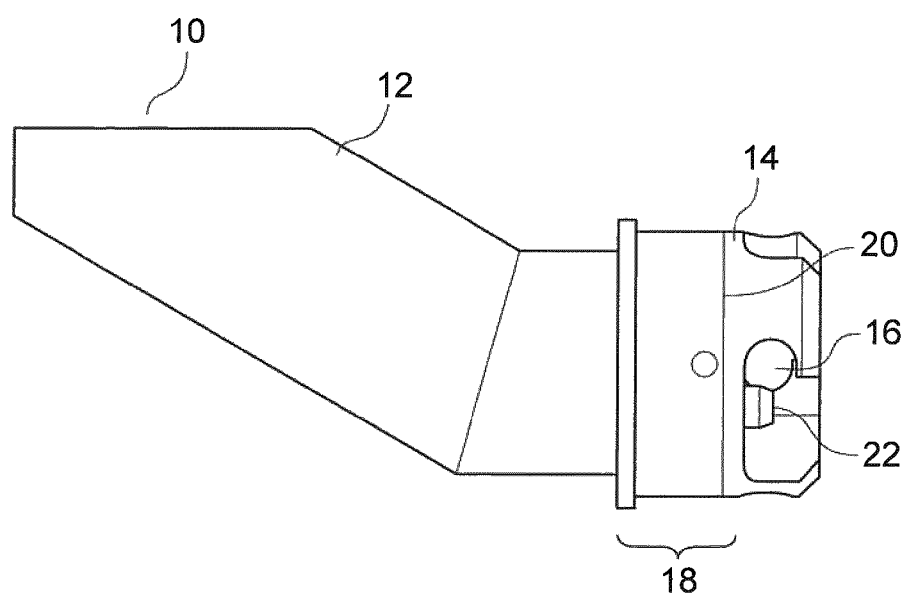
FIG. 1: Shows a side view of a distal tool coupling end of an offset reamer handle.

Referring now to FIG. 1, there is shown a side view of the distal end of an offset reamer handle 10. The handle includes a shank 12 with a distal tool coupling end 14. The distal coupling end is configured to releasably couple to a part of a surgical tool. The distal tool coupling end may be a bayonet-type fitting, as illustrated.

An example of a surgical tool that is adapted to be coupled to the reamer handle is an acetabular grater with cross-bars dimensioned to be received within the slots 16 of the bayonet fitting. Another example, is an acetabular grater with a bridge-back coupling dimensioned to be received within the slots 16 of the bayonet fitting.

The shank also includes a distally located retractable catch, here shown in the form of an annular collar 18. This collar may include circumferential grooves 19, which provide an improved grip functionality. The collar is linearly displaceable along the shank 12 between a non-retracted position, in which the catch captures the surgical tool within the distal tool coupling end 14 of the tool holder and a retracted position, in which the tool may be released. The collar is biased towards the non-retracted position.

Figure 2A:
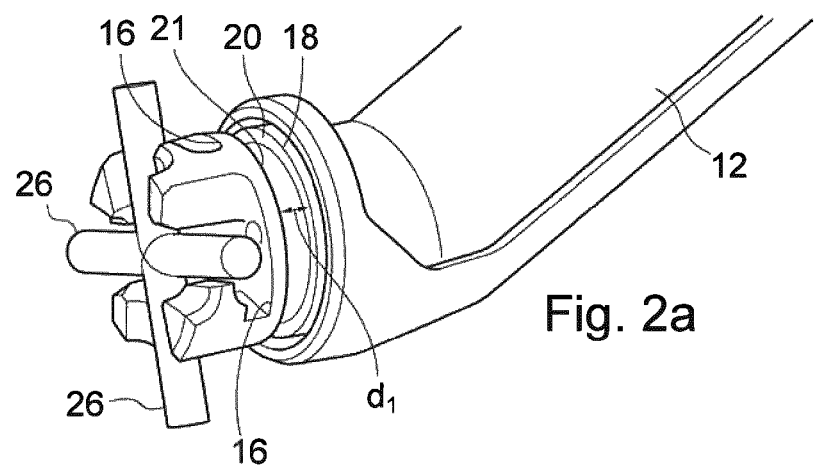
FIGS. 2a-c: Is a schematic of the engagement of an acetabular grater to the distal coupling end of the reamer handle of FIG. 1.
Figure 2B:
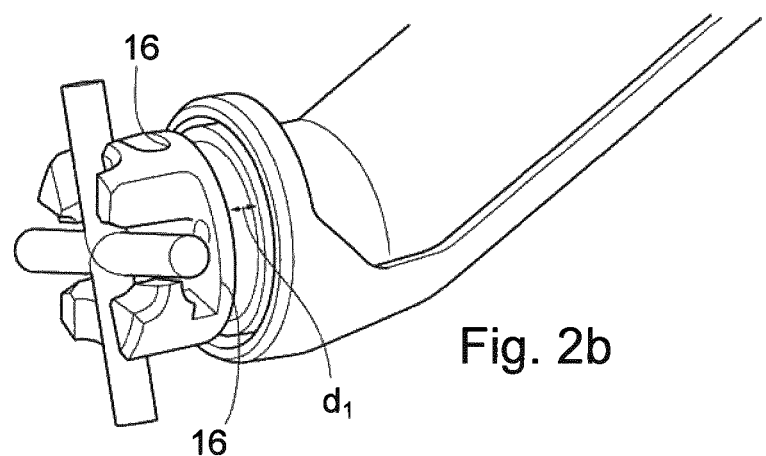
Figure 2C:
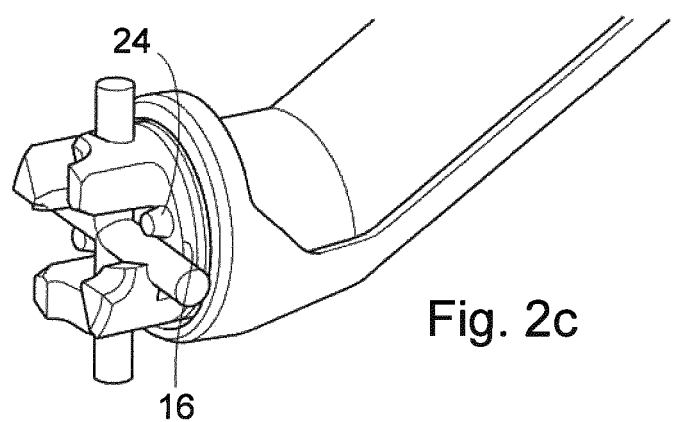

The collar 18 includes substantially disc-shaped distal face 20 from which a centrally-located projection 22 extends. In other constructions of the collar, four projections 24 are circumferentially spaced about the disc-shaped distal face 20 (as shown in FIGS. 2a-2c). The positioning of the projection(s) in relation to the slots 16 of the bayonet-fitting defines whether the acetabular grater is captured within the distal end of the reamer handle or is releasable from the distal end of the reamer handle, as discussed further below with reference to FIG. 2.

As shown in FIG. 2a-c, when the collar 18 is in a retracted position there is a distance $d_1$ between the distal face 20 of the collar and the proximal face 21 of the bayonet-fitting. In this retracted position, the distal end of each projection 22, 24 is moved proximally out of the bayonet-fitting. This enables the cross-bars 26 of the acetabular grater to be aligned with the slots 16 of the bayonet-fitting.

When a user releases his/her grip on the collar 18, it will be returned to its original non-retracted position. The gap (i.e., distance $d_1$) between the distal face 20 of the collar and the proximal face 22 of the bayonet-fitting is partially or completely closed. The acetabular grater is then captured in the bayonet-fitting by virtue of the projection(s) 22, 24 preventing the cross-bars from being rotated out of the slots 16.

Figure 3:
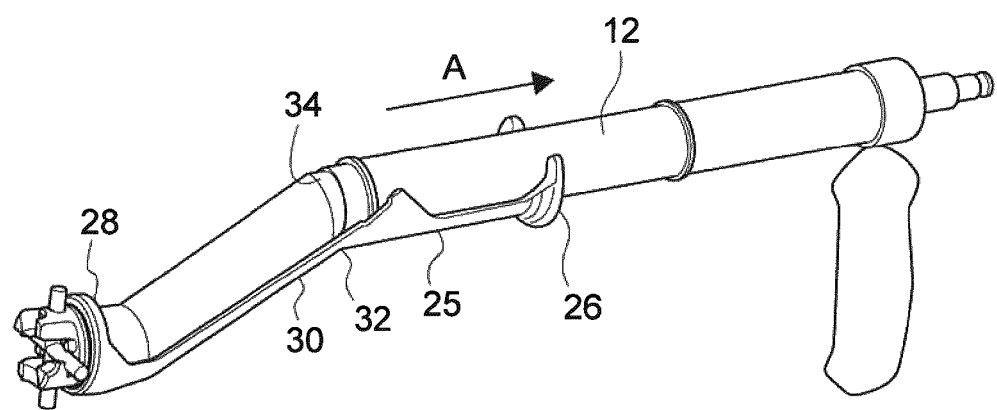
FIG. 3: shows a perspective view of a first construction of the sleeve assembled on an offset reamer handle.
Figure 4A:
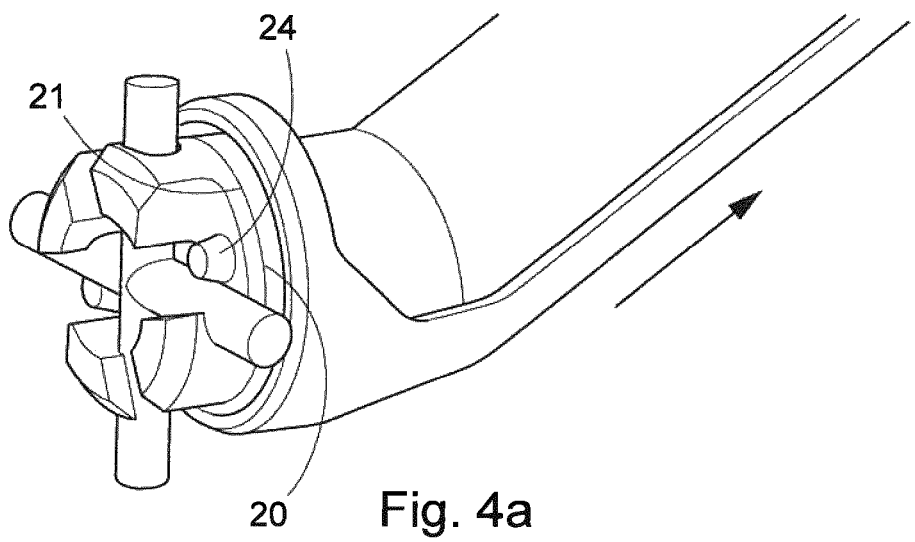
FIGS. 4a-b: Show the first construction of the sleeve assembled onto an offset reamer handle. The retractable catch is illustrated in the non-retracted position (FIG. 4a), and the retracted position (FIG. 4b). The acetabular grater (not shown) is captured within the distal coupling end.
Figure 4B:
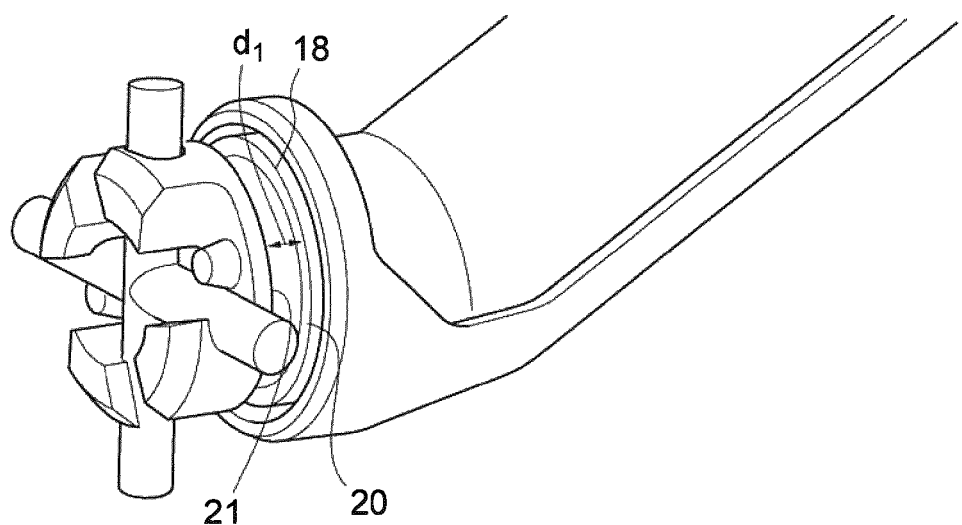

Now referring to FIGS. 3 and 4 there is shown a first construction of the sleeve of the present invention attached to an offset reamer handle of FIG. 1. The sleeve 25 includes a proximally located handle portion 26 for manually displacing the sleeve relative to the shank. As shown, this handle portion can be in the form of semi-annular flange.

The sleeve also includes a distally located catch contacting portion 28. Here, the catch contacting portion is shown in the form of a ring. The ring 28 has an inner circumference that is slightly greater than the outer circumference of the collar 18. Accordingly, the ring 28 encircles at least part of the outer circumference of the collar in a "snug fit" relationship.

A bridge portion 30 extends between the proximally located handle portion 26 and the distally located catch contacting portion 28. The bridge portion in this specific construction of the sleeve has a semi-circular trough-like profile. This part of the sleeve only partially wraps around the shank 12 of the reamer handle 10. This significantly reduces the footprint of the sleeve. The bridge portion also includes a bend 32 which corresponds to the bend 34 in the reamer handle. Bend 34 is formed at the junction between the outer tube 36 and the inner tube 38 and provides the offset.

To remotely activate the acetabular grater release mechanism, the user applies a proximally-directed linear force (along the direction of arrow A) to the handle portion 26. This force is then exerted via the bridge portion 30 to the ring 28. As a result of the coupling between the ring 28 and the collar 18, the collar is in turn displaced from the non-retracted position (to which it is biased) (see FIG. 4a) to the retracted position (see FIG. 4b). A gap (distance $d_1$) is formed between the distal face 20 of the collar and the proximal face 21 of the bayonet-fitting. Consequently, the projections 24 on the collar are moved proximally out of the bayonet-fitting. This provides sufficient clearance for the cross-bars of the acetabular grater to be decoupled from the bayonet fitting, by rotation out of the slots 16.

Figure 5:
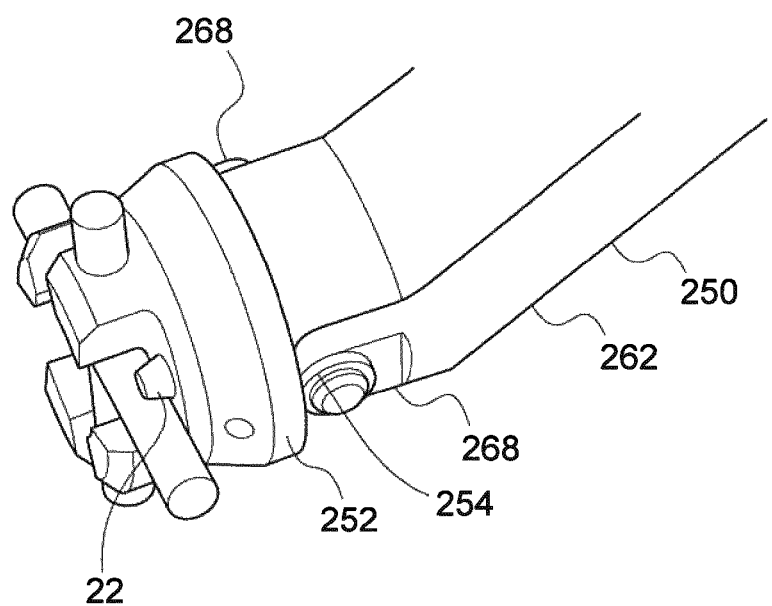
FIG. 5: Shows a detailed view of the retractable catch and the distally-located catch contacting portion of a second construction of the sleeve.

Now referring to FIG. 5, there is shown a second construction of the sleeve 250. In this construction, the surgical tool coupling/decoupling mechanism (i.e., the collar component 18 shown in FIG. 1) on the reamer handle has been replaced. As such, this sleeve is not designed for retrofitting onto conventional reamer handles.

In this modified construction, the conventional collar on the reamer has been removed and replaced by a low-profiled annular catch component 252 and an internal latching component 254.

Figure 6:
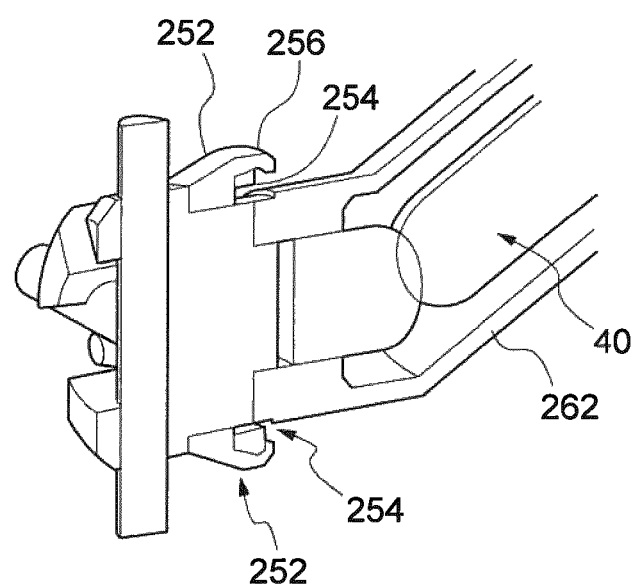
FIG. 6: Shows a cross-sectional view of the second construction of the sleeve shown in FIG. 5.

As shown in FIG. 6, the catch component 252 replaces the collar component. The catch component 252 in the illustrated construction takes the form of a substantially circular ring-like structure. The catch component is connected to the driveline of the reamer handle by a transverse pin. The interior surface of the catch component includes a circumferential groove 256.

The internal latching component 254 (i.e., the sleeve's distally-located catch-contacting portion) is configured to be removably received within the circumferential groove 256 of the catch component 252. In the construction shown, the internal latching component 254 takes the form of a substantially circular ring-like structure. The internal latching component 254 can be snapped-fitted into the circumferential groove 256 of the catch component 252.

Figure 7:
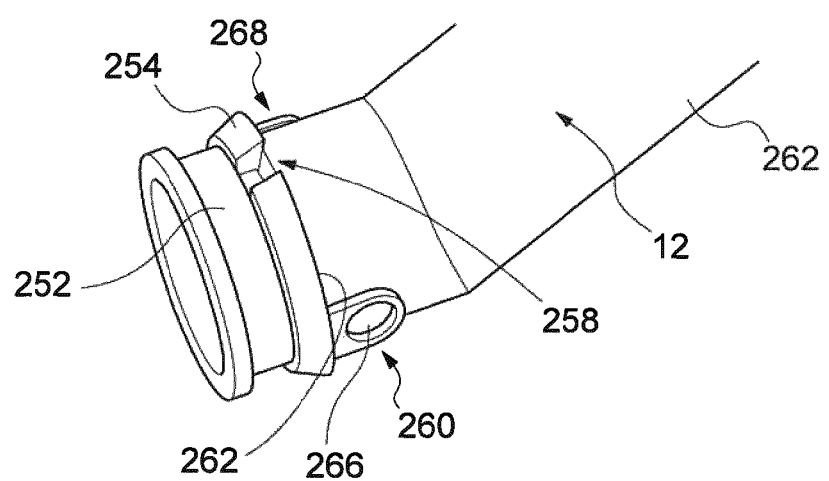
FIG. 7: Shows a detailed view of the distally-located catch contacting portion of a second construction of the sleeve as shown in FIG. 5.
Figure 8:
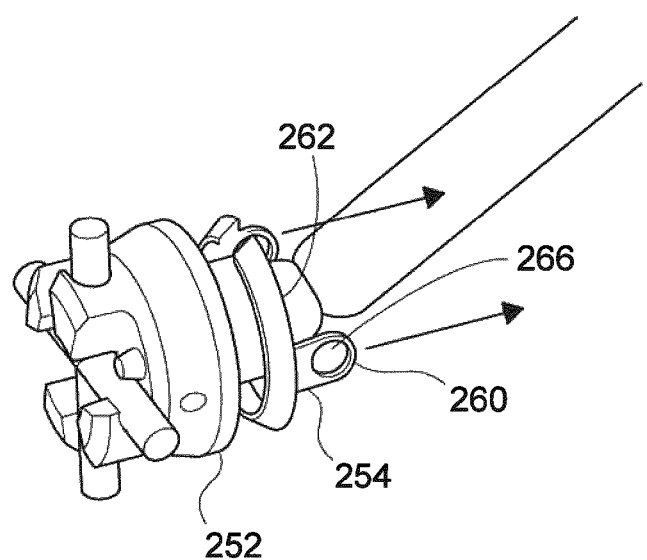
FIG. 8: Shows the disassembly of the distally-located catch contacting portion of the second construction of the sleeve from the retractable catch.

Details of the internal latching component 254 are shown in FIGS. 7 and 8. The component is an incomplete ring. An interruption in the form of a gap 258 in the circumferential extent of the ring facilitates disassembly from the catch component 252 by compressing the ring such that the gap 258 is closed. Disassembly of the two components may be desirable to facilitate their cleaning.

As shown in detail in FIGS. 7 and 8, two opposed resilient tabs 260 extend in a proximal direction from the proximal end face 262 of the internal latching component 254. These tabs provide a mechanism for removably connecting the internal latching component 254 to the bridge portion 264 of the sleeve. Each tab includes an aperture 266.

As shown in FIG. 5, the bridge portion 264 of the sleeve has two distally located substantially circular studs 268. Each stud is dimensioned to be received by a complementary aperture 266.

The assembly of the internal latching component 254 within the catch component 252, by snap fitting of the internal latching component within the circumferential groove 256 of the catch component 252, causes the inward flexion of each resilient tab 260. This causes each aperture 266 to slide over its respective stud 268. This forms a demountable hinged connection between the internal latching component 254 and the bridge portion 264.

Figure 9A:
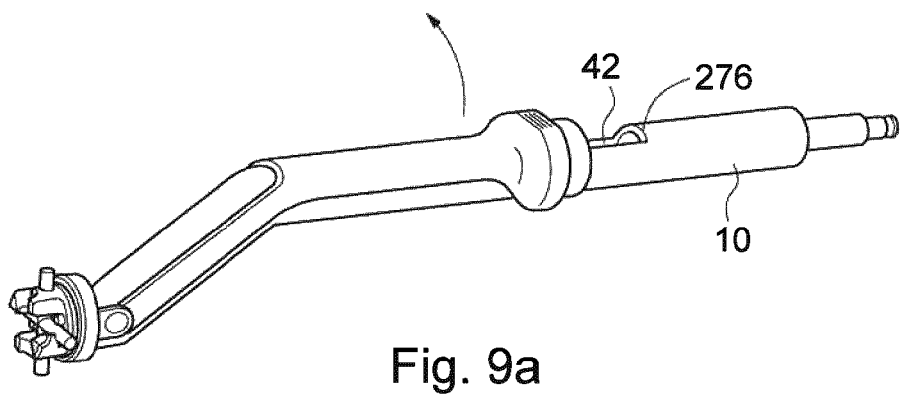
FIG. 9a-c: Shows the process of disassembling the second construction of the sleeve from the reamer handle.
Figure 9B:
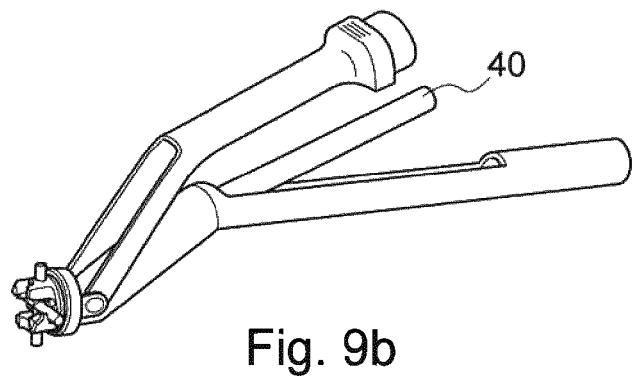
Figure 9C:
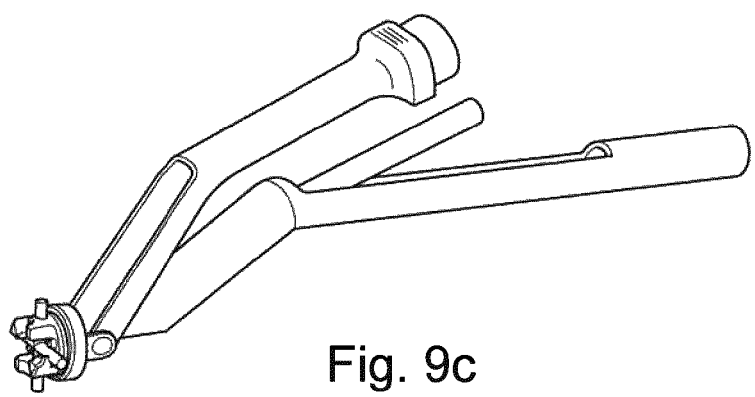

This hinged connection provides a user with the ability to rotate the bridge portion 264 of the sleeve in an anti-clockwise direction away from the shank 12 of the reamer 10 (see FIGS. 9a-c). This enables the user to remove and replace the drive line 40 via the drive line receiving slot 42 which extends through the external surface of the shank. The bridge portion 264 of the sleeve functions as an openable lid for this slot.

The ability to be able to uncouple the bridge portion 264 of the sleeve from the internal latching component 254 at the hinged connection also provides the user with the option of substituting the bridge portion 264 with different designs of bridge portion.

The bridge portion is also provided with a proximally located handle portion 270. The details of which are detailed further below.

The remote activation of the acetabular grater release mechanism for the second construction of the sleeve is substantially the same as has been detailed above in relation to the first construction of the sleeve.

Figure 10:
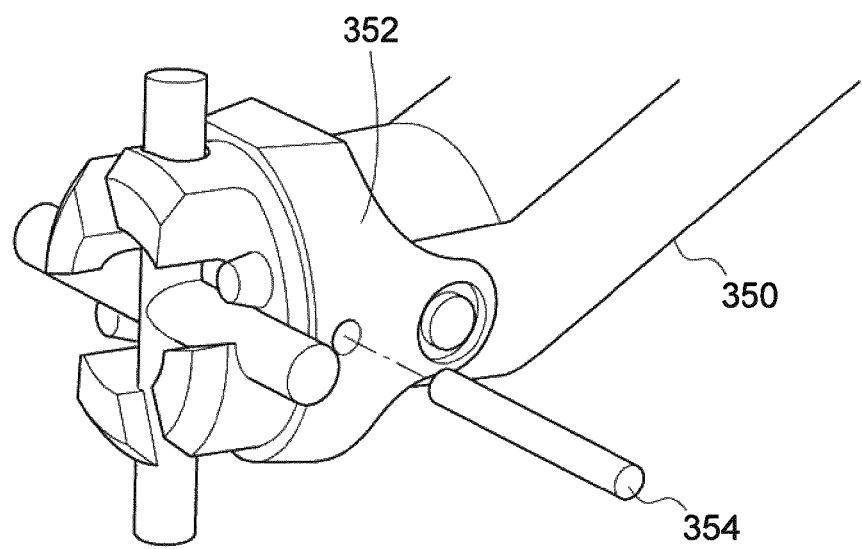
FIG. 10: Shows a detailed view of the retractable catch and the distally-located catch contacting portion of a third construction of the sleeve.
Figure 11:
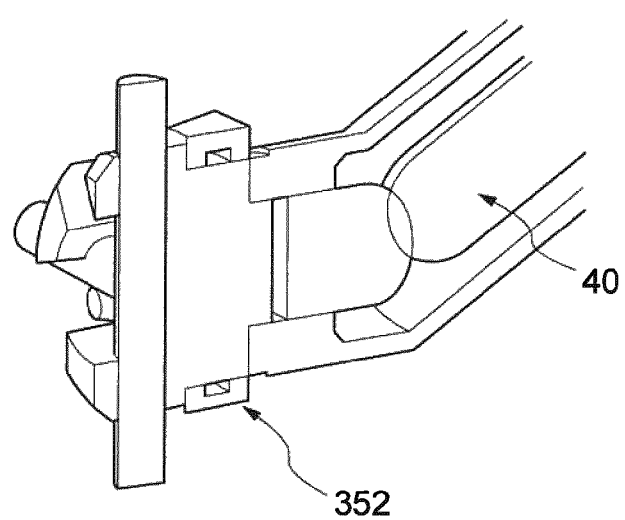
FIG. 11: Shows a cross-sectional view of the third construction of the sleeve shown in FIG. 10.

A third construction of the sleeve 350 is shown in FIG. 10. This construction is similar to that of the second construction of the sleeve, but in this construction the catch component (component 252 in the second construction) and the internal latching component (component 254 in the second construction) are a unitary component 352. This is shown in the cross-sectional view in FIG. 11. This unitary component is pinned to the shank of the reamer handle using a cross-pin 354.

Figure 12:
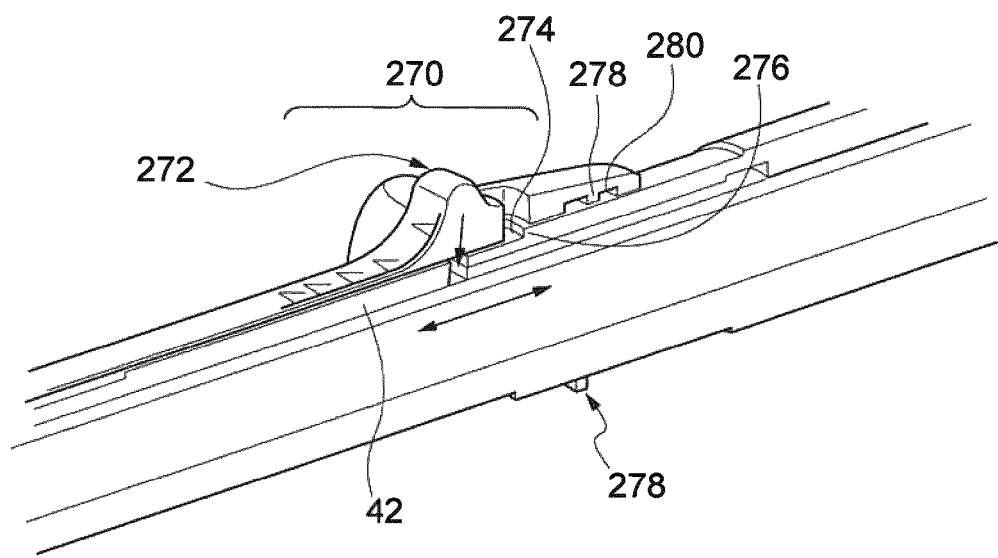
FIG. 12: Shows a detailed view of safety button feature and the stop feature provided on the second and/or third constructions of the sleeve.

Referring now to FIG. 12, the proximally located handle portion 270 of both the second and third constructions of the sleeve is provided with a safety button 272. This safety button prevents the inadvertent remote activation of the retractable catch. Preferably, the safety button is pre-biased in the upward position shown in FIG. 12. Depression of the safety button by the user causes a shoulder element 274 to be moved out of an abutting relationship with a lip 276 of the drive line receiving slot 42. The shoulder element is receivable within and linearly displaceable along the drive line receiving slot.

The proximally located handle portion 270 of both the second and third constructions of the sleeve is also provided with a linear movement restriction device. The linear displacement restriction device includes a stop member 278 in the form of ring extending about the exterior surface of the shank of the reamer handle. This stop member 278 is received within a groove 280 formed within an inward facing surface of the proximally located handle portion 270. The amount of linear movement of the sleeve is restricted by the length (L) of this groove in a direction parallel to the displacement direction of the sleeve. This is because the stop member comes into contact with the opposite edges of the groove to prevent further movement. This prevents overloading of the distal catch portion in both the distal and proximal directions.

Figure 13:
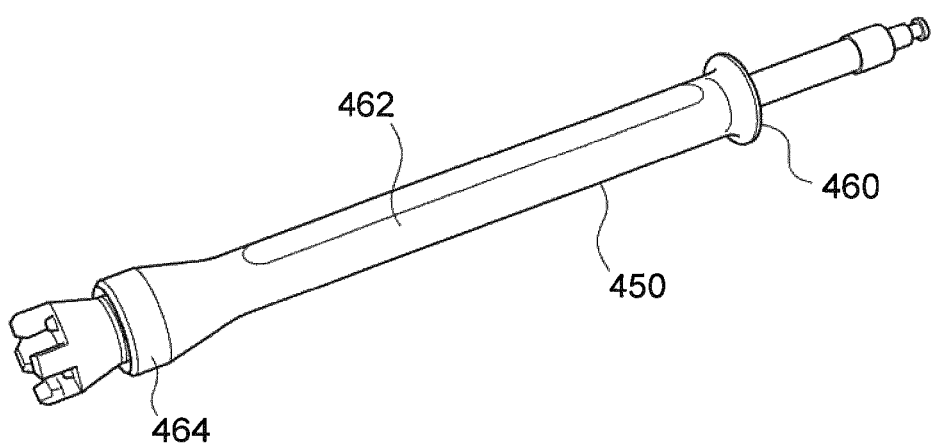
FIG. 13: Shows a fourth construction of the sleeve assembled on a straight reamer handle.

The sleeves 25, 250, 350 discussed above are configured for use with an offset reamer. The sleeve 450 shown in FIG. 13 is for retrofitting onto a straight reamer handle. This sleeve 450 is similar to the first construction of the sleeve 25 and includes a proximally located handle portion 460, a bridge portion 462 and a distally located catch contacting portion 464.

The proximally located handle portion 460 takes the form of a substantially annular flange.

The bridge portion 462 wraps around the entirety of the shank of the reamer handle.

The distally located catch contacting portion 464 is shown in the form of an annular ring. The annular ring 466 has an inner circumference that is slightly greater than the outer circumference of the annular collar (not shown). Accordingly, the annular ring 466 encircles the outer circumference of the collar in a "snug fit" relationship.

Although particular constructions of the invention have been described, it will be appreciated that many modifications/additions and/or substitutions may be made within the scope of the claimed invention.

The invention claimed is:

1. A reamer handle comprising: a shank having a distal tool coupling end adapted to releasably couple to a part of a surgical tool and a proximal end: a retractable catch which is linearly displaceable along the shank between a non-retracted position in which the catch captures the surgical tool within the distal tool coupling end of the tool holder and a retracted position in which the catch enables the tool to be released from the distal tool coupling end: a biasing member configured to bias the catch in the non-retracted position; and a sleeve extending along the shank, the sleeve comprising:

a distally located catch contacting portion and a proximally located handle portion for manually displacing the sleeve relative to the shank such that displacement of the catch contacting portion moves the retractable catch between the non-retracted position and the retracted position to enable capture and release of the tool from the tool holder, in which the shank has at least one bend and the sleeve includes a corresponding bend.

2. The reamer handle of claim 1, in which the retractable catch comprises a collar and the distally located catch contacting portion of the sleeve contacts at least part of the collar.

3. The reamer handle of claim 2, in which the collar is substantially annular and the distally located catch contacting portion of the sleeve is substantially annular.

4. The reamer handle of claim 3, in which the distally located catch contacting portion of the sleeve encircles at least a part of the collar.

5. The reamer handle of claim 2, in which the collar has a shank facing surface and in which the distally located catch contacting portion of the sleeve contacts at least part of the shank facing surface of the collar.

6. The reamer handle of claim 5, in which the shank facing surface of the collar comprises a groove and in which the distally located catch contacting portion of the sleeve is adapted to engage within the groove.

7. The reamer handle of claim 6, in which the groove extends circumferential about at least a part of the shank facing surface.

8. The reamer handle of claim 6, in which the distally located catch contacting portion is removably attached to a distal end of the sleeve.

9. The reamer handle of claim 1, in which the proximally located handle portion comprises a reamer handle coupling feature.

10. The reamer handle of claim 9, in which the reamer handle coupling feature is a snap-fit coupling.

11. The reamer handle of claim 10, in which the snap-fit coupling comprises a flexible clip.

12. The reamer handle of claim 10, in which the flexible clip comprises a semi-circular flange.

13. The reamer handle of claim 12, in which the first portion consists of the distally located catch contacting portion.

14. The reamer handle of claim 1, in which the sleeve comprises a first portion and a second portion and in which the first and second portions are connected by a hinge.

15. The reamer handle of claim 1, in which the sleeve includes a cut out portion.

16. The reamer handle of claim 1, in which at least part of the sleeve is made of a plastic.

17. The reamer handle of claim 1, in which the shank has a central axis and in which the sleeve is linearly displaceable along the central axis.

18. The reamer handle of claim 1, in which the cutting tool is an acetabular grater.

\* \* \* \* \*